United States Patent
Yin et al.

(10) Patent No.: US 9,474,278 B2
(45) Date of Patent: Oct. 25, 2016

(54) BIOCIDAL COMPOSITIONS AND METHODS OF USE

(71) Applicant: Dow Global Technologies LLC, Midland, MI (US)

(72) Inventors: Bei Yin, Buffalo Grove, IL (US); Michael V. Enzien, Lisle, IL (US); Donald J. Love, Midland, MI (US); Emerentiana Sianawati, Vernon Hills, IL (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 0 days.

(21) Appl. No.: 14/351,360

(22) PCT Filed: Oct. 9, 2012

(86) PCT No.: PCT/US2012/059317
§ 371 (c)(1),
(2) Date: Apr. 11, 2014

(87) PCT Pub. No.: WO2013/055665
PCT Pub. Date: Apr. 18, 2013

(65) Prior Publication Data
US 2014/0249114 A1    Sep. 4, 2014

Related U.S. Application Data

(60) Provisional application No. 61/546,585, filed on Oct. 13, 2011.

(51) Int. Cl.
*A01N 57/34* (2006.01)
*A01N 43/80* (2006.01)
*A01N 57/20* (2006.01)
*C02F 1/50* (2006.01)

(52) U.S. Cl.
CPC ............... *A01N 43/80* (2013.01); *A01N 57/20* (2013.01); *A01N 57/34* (2013.01); *C02F 1/50* (2013.01)

(58) Field of Classification Search
None
See application file for complete search history.

(56) References Cited

U.S. PATENT DOCUMENTS

| | | | |
|---|---|---|---|
| 4,673,509 A | 6/1987 | Davis et al. | |
| 5,741,757 A | 4/1998 | Cooper et al. | |
| 6,784,168 B1 | 8/2004 | Jones et al. | |
| 2003/0228373 A1 | 12/2003 | Ludensky et al. | |
| 2010/0286096 A1* | 11/2010 | Yin | A01N 57/20 514/126 |

FOREIGN PATENT DOCUMENTS

| | | | |
|---|---|---|---|
| EP | 0380359 A1 | | 8/1990 |
| GB | 2145708 A | * | 4/1985 |
| WO | 2005074688 A2 | | 8/2005 |
| WO | 2009015088 A2 | | 1/2009 |
| WO | 2009015089 A2 | | 1/2009 |
| WO | 2011016909 A1 | | 2/2011 |

* cited by examiner

*Primary Examiner* — San-Ming Hui
*Assistant Examiner* — Andrew Lee
(74) *Attorney, Agent, or Firm* — Tifani M. Edwards

(57) ABSTRACT

Provided are biocidal compositions comprising: a hydroxymethyl-substituted phosphorus compound and an isothiazolinone compound selected from 1,2-benzisothiazolin-3-one, 2-methyl-1,2-benzisothiazolin-3-one, and mixtures thereof. The compositions are useful for controlling microorganisms in aqueous or water-containing systems.

5 Claims, No Drawings

BIOCIDAL COMPOSITIONS AND METHODS OF USE

BACKGROUND

The invention relates generally to biocidal compositions and methods of their use for the control of microorganisms in aqueous and water-containing systems. The compositions comprise a hydroxymethyl-substituted phosphorus compound and an isothiazolinone compound selected from 1,2-benzisothiazolin-3-one, 2-methyl-1,2-benzisothiazolin-3-one, and mixtures thereof.

Protecting water-containing systems from microbial contamination is critical to the success of many industrial processes, including oil or natural gas production operations. In oil and gas operations, microorganism contamination from both aerobic and anaerobic bacteria can cause serious problems such as reservoir souring (mainly caused by anaerobic sulfate-reducing bacteria (SRB)), microbiologically influenced corrosion (MIC) on metal surfaces of equipment and pipelines, and degradation of polymer additives.

Biocides are commonly used to control the growth of microorganisms in aqueous and water containing systems. However, not all biocides are effective against a wide range of microorganisms, particularly when used at low concentrations. In addition, some biocides do not provide microbial control over long enough time periods, or alternatively are effective over long time periods, but not short time periods.

While some of these shortcomings can be overcome through use of larger amounts of the biocide, this option creates its own problems, including increased cost, increased waste, and increased likelihood that the biocide will interfere with the desirable properties of the treated medium. In addition, even with use of larger amounts of the biocide, many commercial biocidal compounds cannot provide both short term and long term effectiveness.

The problem addressed by this invention is the provision of biocides that are effective against a wide range of microorganisms, that may be used in reduced amounts so as to be economically and environmentally attractive, and/or that are effective for both short term and long term control of microorganisms.

STATEMENT OF INVENTION

In one aspect, the invention provides biocidal compositions. The compositions are useful for controlling microbial growth in aqueous or water-containing systems, including for applications in the oil and natural gas industry. The compositions of the invention comprise: a hydroxymethyl-substituted phosphorus compound selected from the group consisting of a tetrakis(hydroxymethyl)phosphonium salt, a $C_1$-$C_3$ alkyl- or $C_2$-$C_3$ alkenyl-tris(hydroxymethyl)phosphonium salt, and tris(hydroxymethyl)phosphine; and an isothiazolinone compound selected from 1,2-benzisothiazolin-3-one, 2-methyl-1,2-benzisothiazolin-3-one, and mixtures thereof.

In a second aspect, the invention provides a method for controlling microorganisms in aqueous or water-containing systems. The method comprises treating the system with an effective amount of a biocidal composition as described herein.

DETAILED DESCRIPTION

As noted above, the invention provides biocidal compositions and methods of using them in the control of microorganisms. The compositions comprise a hydroxymethyl-substituted phosphorus compound and an isothiazolinone compound selected from 1,2-benzisothiazolin-3-one, 2-methyl-1,2-benzisothiazolin-3-one, and mixtures thereof. It has surprisingly been discovered that combinations of a hydroxymethyl-substituted phosphorus compound and the isothiazolinone compound as described herein, at certain weight ratios, are synergistic when used for microorganism control in aqueous or water-containing media. That is, the combined materials result in improved biocidal properties than would otherwise be expected based on their individual performance at the particular use-concentration. The observed synergy permits reduced amounts of the materials to be used to achieve acceptable biocidal properties.

In addition to exhibiting synergy, the compositions of the invention are effective at providing both short term (2 hours or less) and long term (14 days or more) control of microorganisms. As a result of these attributes, the compositions are well suited for use in various applications, including in the oil and natural gas industry where biocidal agents are needed that are capable of controlling microorganisms over both the short and the long term.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation against microorganism growth.

The composition of the invention comprises: a hydroxymethyl-substituted phosphorus compound and a isothiazolinone compound selected from 1,2-benzisothiazolin-3-one, 2-methyl-1,2-benzisothiazolin-3-one, and mixtures thereof.

The hydroxymethyl-substituted phosphorus compound for use in the invention is selected from the group consisting of a tetrakis(hydroxymethyl)phosphonium salt, a $C_1$-$C_3$ alkyl- or $C_2$-$C_3$ alkenyl-tris(hydroxymethyl)phosphonium salt, and tris(hydroxymethyl)phosphine. Such compounds are generally available both in undissolved form or as aqueous solutions. In one embodiment of the invention, the hydroxymethyl-substituted phosphorus compound is a tetrakis(hydroxymethyl)-phosphonium salt, such as the chloride, phosphate, or sulfate salt. A preferred compound is tetrakis (hydroxymethyl) phosphonium sulfate (THPS). THPS is available from The Dow Chemical Company as AQUCAR™ THPS 75, a 75 wt % solution in water. Of course, more than one of the recited hydroxymethyl-substituted phosphorus compounds can be combined for use in the present invention; in such cases, ratios and concentrations are calculated using the total weight of all hydroxymethyl-substituted phosphorus compounds.

The isothiazolinone compound of the invention is selected from 1,2-benzisothiazolin-3-one, 2-methyl-1,2-benzisothiazolin-3-one, and mixtures thereof. In some preferred embodiments, the compound is 1,2-benzisothiazolin-3-one. 1,2-Benzisothiazolin-3-one and 2-methyl-1,2-benzisothiazolin-3-one are commercially available or they may be readily prepared by those skilled in the art.

In some embodiments, the isothiazolinone compound is 1,2-benzisothiazolin-3-one and the weight ratio of the hydroxymethyl-substituted phosphorus compound to the 1,2-benzisothiazolin-3-one in the compositions of the invention is between 50:1 and 1:50, alternatively between 20:1 and 1:20, alternatively between 10:1 and 1:10, or alternatively between 8:1 and 1:8. In some embodiments, the weight ratio is between about 8:1 and 4:1. In some embodiments the weight ratio is between about 1:2 and 1:8.

In some embodiments, the isothiazolinone compound is 2-methyl-1,2-benzisothiazolin-3-one and the weight ratio of the hydroxymethyl-substituted phosphorus compound to the 2-methyl-1,2-benzisothiazolin-3-one in the compositions of the invention is between 10000:1 and 5000:1.

The compositions of the invention may contain additional components including, but not limited to, surfactants, stabilizers, demulsifier, polymers, and/or additional biocides.

The compositions of the invention are useful for controlling microorganisms in aqueous or water-containing systems. In some embodiments, the aqueous or water containing system comprises at least 10 weight percent, alternatively at least 20 weight percent, alternatively at least 40 weight percent, alternatively at least 60 weight percent, or alternatively at least 80 weight percent of water. Non-limiting examples of aqueous or water containing systems with which the inventive compositions may be used to control microorganisms include those present in oil and natural gas applications. Examples of such systems include, but are not limited to, injection and produced water, source water for waterflooding and hydraulic fracturing such as pond water and holding tank water, functional fluids such as drilling muds, completion or workover fluids, hydrotest fluids, stimulation fluids, packer fluids, and fracturing fluids, oil and gas wells, separation, storage, and transportation systems, oil and gas pipelines, oil and gas vessels, or fuel.

The inventive compositions may also be used for controlling microorganisms in other industrial aqueous and water containing/contaminated systems, such as cooling water, air washer, heat exchangers, boiler water, pulp and paper mill water, other industrial process water, ballast water, wastewater, metalworking fluids, latex, paint, coatings, adhesives, inks, tape joint compounds, pigment, water-based slurries, swimming pool, personal care and household products such as detergent, membrane and filtration systems, toilet bowel, textiles, leather and leather production system, or a system used therewith.

In some embodiments, the microorganism being controlled with the compositions of the invention is anaerobic, such as SRB. In some embodiments, the microorganism being controlled is anaerobic, such as SRB, and the aqueous system contains a reducing agent, such as sulfide.

In some embodiments, the microorganism controlled by the composition of the invention is yeast, preferably *Candida albican*.

A person of ordinary skill in the art can readily determine, without undue experimentation, the concentration of the composition that should be used in any particular application. By way of illustration, a suitable actives concentration (total for both the hydroxymethyl-substituted phosphorus compound and the isothiazolinone compound) is typically between 1 and 2500 ppm, alternatively between 5 and 1000 ppm, alternatively between 10 and 500 ppm, or alternatively between 50 and 300 ppm, based on the total weight of the aqueous or water-containing system including the biocides. In some embodiments for oil and gas applications, it is preferred that active concentrations of the composition range from about 10 to about 300 ppm by weight, preferably about 30 to 100 ppm, for top side treatment, and from about 30 to about 500 ppm, preferably about 50 to about 250 ppm, for downhole treatment.

The components of the inventive compositions can be added to the aqueous or water-containing system separately, or preblended prior to addition. A person of ordinary skill in the art can easily determine the appropriate method of addition. The composition can be used in the system with other additives such as, but not limited to, surfactants, ionic/nonionic polymers and scale and corrosion inhibitors, oxygen scavengers, and/or additional biocides.

Unless otherwise indicated, numeric ranges, for instance as in "from 2 to 10," are inclusive of the numbers defining the range (e.g., 2 and 10).

Unless otherwise indicated, ratios, percentages, parts, and the like are by weight. The following examples are illustrative of the invention but are not intended to limit its scope. Unless otherwise indicated, ratios, percentages, parts, and the like used herein are by weight.

EXAMPLES

The synergy indexes reported in the following examples are calculated using the following equation:

$$\text{Synergy Index} = Ca/CA + Cb/CB$$

Ca: Concentration of biocide A required to achieve a certain level of bacterial kill when used in combination with B.

CA: Concentration of biocide A required to achieve a certain level of bacterial kill when used alone.

Cb: Concentration of biocide B required to achieve a certain level of bacterial kill when used in combination with A.

CB: Concentration of biocide B required to achieve a certain level of bacterial kill when used alone.

A synergy index (SI) of 1 indicates additivity, a synergy index of less than 1 indicates synergy, and a synergy index greater than 1 indicates antagonism.

Example 1

Synergistic Effect of tetrakis (hydroxymethyl) phosphonium sulfate (THPS) and 1,2-benzisothiazolin-3-one (BIT)

A sterile salt solution (0.2203 g of $CaCl_2$, 0.1847 g of $MgSO_4$, and 0.2033 g of $NaHCO_3$ in 1 L water) is inoculated with approximately $10^7$ CFU/mL of *Staphylococcus aureus* ATCC 6538, *Enterobacter aerogenes* ATCC 13048, and *Escherichia coli* ATCC 8739. Aliquots of the cell suspension are then treated with THPS, BIT, and combinations of these actives at selected concentrations and incubated at 37° C. for 14 days. After incubation for 24 hours, 3 days, and 7 days, the aliquots are re-challenged with bacterial suspension of the same bacteria at a final bacterial concentration of $10^5$ CFU/mL. The biocidal efficacy is measured at 2 hours and 14 days by determining the minimum biocide concentration for 99.9% bacterial kill in the aliquots. Synergy Index is then calculated. Table 1 and 2 summarize the efficacy of each biocide and their combinations at 2 hour and 14 day treatment time respectively, and the resulting Synergy Index of each combination.

TABLE 1

Biocidal efficacy of THPS, BIT, THPS/BIT combinations after 2 hour treatment, and resulting Synergy Index.

| Active weight ratio of THPS:BIT | Concentration (ppm active) for 99.9% bacterial kill in 2 hours | | Synergy Index |
|---|---|---|---|
| | THPS | BIT | |
| 1:0 | 38 | 0 | |
| 8:1 | 33 | 4 | <0.90 |

TABLE 1-continued

Biocidal efficacy of THPS, BIT, THPS/BIT combinations after 2 hour treatment, and resulting Synergy Index.

| Active weight ratio of THPS:BIT | Concentration (ppm active) for 99.9% bacterial kill in 2 hours | | Synergy Index |
|---|---|---|---|
| | THPS | BIT | |
| 4:1 | 30 | 8 | <0.83 |
| 2:1 | 50 | 25 | <1.42 |
| 1:2 | >100 | >200 | NA |
| 1:4 | >60 | >240 | NA |
| 1:8 | >33 | >267 | NA |
| 0:1 | | >300 | |

TABLE 2

Biocidal efficacy of THPS, BIT, THPS/BIT combinations after 14 day treatment, and resulting Synergy Index

| Active weight ratio of THPS:BIT | Concentration (ppm active) for 99.9% bacterial kill in 14 days | | Synergy Index |
|---|---|---|---|
| | THPS | BIT | |
| 1:0 | >300 | | |
| 8:1 | 267 | 33 | <1.11 |
| 4:1 | 240 | 60 | <1.20 |
| 2:1 | 200 | 100 | <1.33 |
| 1:2 | 50 | 100 | <0.67 |
| 1:4 | 30 | 120 | <0.90 |
| 1:8 | 8 | 67 | <0.47 |
| 0:1 | | 150 | |

As shown in Table 1 and Table 2, THPS in combination with BIT has synergistic effect against tested bacteria for both short term and extended treatment period.

Example 2

Synergistic Effect of tetrakis (hydroxymethyl) phosphonium sulfate (THPS) and 2-methyl-1,2-benzisothiazolin-3-one (MBIT)

Synergy tests of MBIT and THPS are conducted using standard 96 well micro titer plate assay with media design for the optimal growth of the test microorganisms. For yeast (Candida albican, ATCC #10231) testing, SDB (Sabouraud Dextrose Broth) is used. The minimum inhibitory concentration (MIC) of biocides blends is performed by adding 170 uL of SDB, 10 µl of tested organism and 10 µl of each biocides into the 64 of the 96 well plate. The final biocides and test inoculum concentrations in each well are established based on this total volume. The final test inoculums concentration are approximately $10^4$ cfu/ml. The highest concentration of MBIT and THPS used in this synergy study is 10 and 4000 ppm respectively. Eight subsequent 2 fold dilutions of each biocide are prepared using automated liquid handling system. The first biocide is added into the well plate horizontally and the second biocide is added after rotating the plate 90 degrees. Columns nine and ten are reserved for each individual biocide to be tested at each concentration level to achieve an active inhibitory end point for synergy index calculation. Columns 11 and 12 are used as positive controls just containing media and the test organism. The plates are incubated at 25□ C for 48 hours or until growth is observed in the control wells. Plates are scored as growth or no growth based on turbidity formation and the lowest passing concentration is recorded.

Ratios of the two biocides exhibiting synergy are presented in Table 3. Synergy of MBIT and THPS against *E. coli* and *Aspergillus niger* was not observed at the tested ratios.

TABLE 3

| Active Weight ratio of MBIT and THPS | Minimum Inhibitory Concentration against *Candida albican* (ppm) | | Synergy Index |
|---|---|---|---|
| | MBIT | THPS | |
| 1:0 | 0.375 | | |
| 0:1 | | 1000 | |
| 1:5,000 | 0.1 | 500 | 0.77 |
| 1:10,000 | 0.05 | 500 | 0.63 |

What is claimed is:

1. A synergistic composition effective against controlling sulfate reducing bacteria comprising tetrakis (hydroxymethyl) phosphonium sulfate and 1,2-benzisothiazolin-3-one in a ratio from 1:2 and 1:8.

2. A method for controlling sulfate reducing bacteria in an aqueous or water-containing system, the method comprising treating the system with the composition claim 1.

3. The method of claim 2 wherein the aqueous or water-containing system is used or is present in oil or gas production.

4. The method of claim 3 wherein oil or gas production comprises injection and produced water, source water for waterflooding and hydraulic fracturing, pond water, holding tank water, functional fluids, drilling muds, completion and workover fluids, hydrotest fluids, stimulation fluids, packer fluids, fracturing fluids, oil and gas wells, separation, storage and transportation systems, oil and gas pipelines, oil and gas vessels, or fuel.

5. The method of claim 2 wherein the aqueous or water-containing system is cooling water, air washer, heat exchangers, boiler water, pulp and paper mill water, other industrial process water, ballast water, wastewater, metalworking fluids, latex, paint, coatings, adhesives, inks, tape joint compounds, pigment, water-based slurries, swimming pool, personal care and household products such as detergent, membrane and filtration systems, toilet bowl, textiles, leather and leather production system, or a system used therewith.

* * * * *